United States Patent [19]

Hsia Chen

[11] Patent Number: 5,095,165

[45] Date of Patent: Mar. 10, 1992

[54] HYDROCARBON LUBRICANTS CONTAINING POLAR GROUPS

[75] Inventor: Catherine S. Hsia Chen, Berkley Heights, N.J.

[73] Assignee: Mobil Oil Corporation, Fairfax, Va.

[21] Appl. No.: 496,836

[22] Filed: Mar. 21, 1990

[51] Int. Cl.$^5$ .............................................. C07C 6/00
[52] U.S. Cl. .................................. 585/643; 585/645; 585/646; 585/647
[58] Field of Search ................. 585/643, 645, 646, 647

[56] References Cited

U.S. PATENT DOCUMENTS

| | | | |
|---|---|---|---|
| 3,723,563 | 3/1973 | Bradshaw | 585/646 |
| 4,520,221 | 5/1985 | Chen | 585/517 |
| 4,568,786 | 2/1986 | Chen et al. | 585/517 |
| 4,658,079 | 4/1987 | Chen | 585/517 |
| 4,665,245 | 5/1987 | Quann | 585/316 |
| 4,827,064 | 5/1989 | Wu | 585/10 |
| 4,827,073 | 5/1989 | Wu | 585/530 |

FOREIGN PATENT DOCUMENTS 644766  10/1976  U.S.S.R. ............... 585/646

OTHER PUBLICATIONS

Mol, "Metathesis of Functionalized Olefins", J. Molecular Catalysis, vol. 15 (1982) pp. 35-45.
Olefin Metathesis, Chapter 7, by K. J. Ivin.
Van Dam, Chem. Soc., Chem Comm., p. 1221, 1972.
Olefin Metathesis and Ring-Opening Polymerization of Cyclo-Olefins, pp. 110-113, by V. Dragutan (J. Wiley & Son).
Kirk Otmer, vol. 14, pp. 477-526, third edition.

Primary Examiner—Asok Pal
Attorney, Agent, or Firm—Alexander McKillop; Charles J. Speciale; L. G. Wise

[57] ABSTRACT

The invention discloses that hydrocarbon lubricants containing olefinic unsaturation participate in an olefin metathesis reaction with alkenes containing polar functional groups to provide an equilibrium mixture containing hydrocarbon lubricants containing the polar groups of the alkenes. The discovery is particularly applicable to the functionalization of near linear lubricants prepared from the oligomerization of propylene using surface deactivated zeolite or lubricants prepared by the oligomerization of $C_6$-$C_{20}$ alpha olefins using coordination catalyst. Functionalized groups can be incorporated that impart a wide range of properties to the lubricant such as anti-wear or anti-corrosion resistance, or improve the compatibility of the lubricant with other additives.

20 Claims, No Drawings

HYDROCARBON LUBRICANTS CONTAINING POLAR GROUPS

This invention relates to a process for the production of synthetic hydrocarbon lubricants containing polar functional groups by co-metathesis between olefinic hydrocarbon lubricants and alkenes containing polar groups. The invention particularly relates to a process for incorporating useful functional groups into lubricants derived from zeolite catalyzed oligomerization of light olefins or polyalphaolefins prepared by cationic or coordination catalysis.

BACKGROUND OF THE INVENTION

The formulation of lubricants typically includes an additive package incorporating a variety of chemicals to improve or protect lubricant properties in application specific situations, particularly internal combustion engine and machinery applications. The more commonly used additives include oxidation inhibitors, rust inhibitors, antiwear agents, pour point depressants, detergent-dispersants, viscosity index (VI) improvers, foam inhibitors and the like. This aspect of the lubricant arts is specifically described in Kirk-Othmer "Encyclopedia of Chemical Technology", 3rd edition, Vol. 14, pp477-526, incorporated herein by reference. The inclusion of additives in lubricants provides a continuing challenge to workers in the field to develop improved additives of increased compatibility with the lubricant and other additives or new additives containing a multifunctional capability that can reduce the number of additives required in the formulation.

Considering the diversity of chemical structures represented by the plethora of additives incorporated in a typical lubricant formulation, and the quantity in which they are added, the artisan in the lubricant formulation arts faces a substantial challenge to provide a homogeneous formulation which will remain stable or in solution during inventory and during use. Lubricants, particularly synthetic lubricants of the type of interest in the instant invention, are usually hydrogenated olefins containing, optionally, mineral oil, ester lubricants and the like. Due to their hydrocarbon structure they are largely incompatible with polar additives such as antioxidants, antirust and antiwear agents, etc. Accordingly, in order to render the lubricants compatible with the polar additives large amounts of expensive polar organic esters must be added to the formulation. Useful commercial formulations may contain 20 percent or more of such esters as bis-tridecanol adipate or pentaerythritol hexanoate for example, primarily to provide a fully homogeneous lubricant blend of lubricant and additive.

Modifying the solvent properties of lubricants with solubilizing agents such as organic esters, while solving the problem of how to prepare stable blends with lubricant additives, creates or accentuates other performance related problems beyond the added burden of cost on the product. Accordingly, workers in the field seek to incorporate the desirable properties of additives into lubricants, without incurring the usual physical and cost liabilities. One approach is to incorporate polar functional groups into the lubricant molecule to thereby include the additive property inherent in that functional group or render the lubricant more compatible with polar additives.

One class of lubricants of particular interest in the present invention is synthetic lubricants obtained by the oligomerization of olefins, particularly $C_3-C_{20}$ alpha olefins. Catalytic oligomerization of olefins has been studied extensively. Known olefin oligomerization catalysts include the Ziegler-Natta type catalysts and promoted catalysts such as $BF_3$ or $AlCl_3$ catalysts. U.S. Pat. No. 4,613,712 for example, teaches the preparation of isotactic alpha-olefins in the presence of a Ziegler type catalyst. Other coordination catalysts, especially chromium on a silica support, are described in the art. Of notable importance is the inventions described in U.S. Pat. Nos. 4,827,064 and 4,827,073 to M. Wu, incorporated herein by reference, where superior hydrocarbon lubricants are prepared having low methyl to methylene branch ratio by oligomerization of alpha olefins using reduced valence state Group VIB metal oxide catalyst on porous support. Also, U.S. Pat. Nos. 4,520,221, 4,568,786 and 4,658,079 to C. S. H. Chen et al., incorporated herein by reference in their entirety, disclose further advances in zeolite catalyzed olefin oligomerization to produce lubricants. These patents disclose processes for the oligomerization of light, or lower, olefins using zeolite catalyst such as ZSM-5.

The foregoing synthetic lubricants contain olefinic unsaturation as prepared by oligomerization of $C_3-C_{20}$ olefins. This unsaturation provides a convenient site for the functionalization of these lubricants to augment their lubricant properties or enhance their compatibility with additives. The olefin bond in these lubricants can participate in a wide range of typically olefin reactions, including olefin metathesis. Olefin metathesis is well known in the art and is described in *Olefin Metathesis* by K.J.Ivin, published by Academic Press, wherein Chapter 7, incorporated herein by reference, describes olefin metathesis with acyclic unsaturated compounds containing functional groups. As described therein, it is known that unsaturated esters as well as other olefinic compounds containing polar groups can participate in the olefin metathesis reaction to provide an equilibrium mixture of functionalized olefins.

It is an object of the present invention to provide a process for the functionalization of unsaturated synthetic lubricants by olefin metathesis with alkenes containing polar groups.

Another object of the present invention is to provide a process for the production of lubricants containing property enhancing polar groups.

Yet another object of the invention is to provide novel lubricant mixtures from conventional lubricants and additive quantities of synthetic lubricants functionalized by olefin metathesis.

SUMMARY OF THE INVENTION

The discovery has been made that hydrocarbon lubricants containing olefinic unsaturation will participate in an olefin metathesis reaction with alkenes containing polar functional groups to provide an equilibrium mixture containing hydrocarbon lubricants containing the polar groups of the alkenes. The discovery is particularly applicable to the functionalization of lubricants prepared from the oligomerization of propylene using surface deactivated zeolite or lubricants prepared by the oligomerization of $C_6-C_{20}$ alpha olefins using coordination catalyst. Functionalized groups can be incorporated that impart a wide range of properties to the lubricant such as anti-wear or anti-corrosion resistance, or improve the compatibility of the lubricant with other additives.

More particularly, a process has been discovered for the production of hydrocarbon lubricant fluid containing one or more polar functional groups. The process comprises contacting a feedstock comprising olefinic hydrocarbon lubricant and at least one alkene containing a polar organic or organometallic functional group with olefin metathesis catalyst under olefin metathesis reaction conditions for a time sufficient to convert a portion of said olefinic hydrocarbon lubricant to one containing said polar functional group. The product is separated and a mixture recovered comprising said hydrocarbon lubricant fluid containing at least one polar functional group. Preferably, the olefinic hydrocarbon lubricant comrpises $C_{20}+$ hydrocarbons from the reaction product of $C_3-C_{20}$ alpha olefins in contact with cationic, coordination or acidic shape selective zeolite catalyst; particularly, surface deactivated ZSM-5 or ZSM-23.

The functionalized lubricants can be mixed with synthetic lubricants or mineral oil lubricants to improve the performance of those lubricants, largely as a result of the effect of the incorporated polar group on the mixture.

DETAIL DESCRIPTION OF THE INVENTION

In the present invention olefin metathesis is carried out between lubricant grade olefinic hydrocarbons and an alkene containing one or more polar functional groups, alike or different, according to the general equilibrium reaction

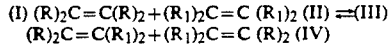
$$(I)\ (R)_2C=C(R)_2+(R_1)_2C=C\ (R_1)_2\ (II) \rightleftharpoons (III)$$
$$(R)_2C=C(R_1)_2+(R_1)_2C=C\ (R)_2\ (IV)$$

wherein R is hydrogen or $C_{20}+$ alkyl or alkenyl with at least one R comprising said $C_{20}+$ alkyl or alkenyl; and wherein $R_1$ is hydrogen, alkyl, alkenyl, aryl, —$CH_2X$ or X with at least one $R_1$ comprising said —$CH_2X$ or X wherein X is a polar functional group. The products of the reaction are useful directly as lubricant additives or they are hydrogenated to saturated olefinic bonds by means well known in the art and utilized as lubricants or lubricant additives.

Olefinic Hydrocarbon Lubricants

The olefinic hydrocarbon lubricants (I) used as starting material in the present invention are obtained from oligomerization of olefins. Olefin oligomerization of 1-alkenes is a particularly useful source of olefinic lubricants for functionalization accordin9 to the present invention. Examples of these include lubricants prepared from the oligomerization of $C_3-C_{20}$ alpha olefins by cationic or coordination catalyst. The oligomerization of 1-alkenes, particularly 1-decene, by Lewis acids such as complexes of $BF_3$ or $AlCl_3$ is well known in the art and produces a polyalphaolefin (PAO) with lubricant properties superior to mineral oil. Coordination catalysts include those of the Ziegler type and reduced chromium oxide. These lubricant oligomerization products contains some olefin bonds.

The oligomerization of light olefins with zeolite catalyst also provides a useful source of lubricant feedstock for functionalization by the process of this invention. In this case, propylene is a preferred olefin for oligomerization with ZSM-5 or with surface deactivated ZSM-5 or ZSM-23 which yields a near-linear product.

The near linear olefin oligomers used as starting material in the present invention are prepared from $C_3-C_5$ olefins according to the methods presented by Chen, et al., in the aforementioned patents cited and N. Page and L. Young in allowed application Serial No. 105,438, filed Oct. 7, 1987 and incorporated herein as references. Shape-selective oligomerization, as it applies to conversion of $C_3-C_5$ olefins over ZSM-5, is known to produce higher olefins up to $C_{30}$ and higher. Reaction conditions favoring higher molecular weight products are low temperature (200°-260° C.), elevated pressure (about 2000 kPa or greater) and long contact times (less than 1 WHSV). The reaction under these conditions proceeds through the acid catalyzed steps of oligomerization, isomerization-cracking to a mixture of intermediate carbon number olefins, and interpolymerization to give a continuous boiling product containing all carbon numbers. The channel system of ZSM-5 type catalysts impose shape selective constraints on the configuration of large molecules, accounting for the differences with other catalysts.

The shape-selective oligomerization/polymerization catalysts preferred for use herein to prepare the olefin oligomers used as starting material in the invention include the crystalline aluminosilicate zeolites having a silica to alumina molar ratio of at least 12, a constraint index of about 1 to 12 and acid cracking activity of about 50-300. Representative of the ZSM-5 type zeolites are ZSM-5, ZSM-11, ZSM-12, ZSM-23, ZSM-35 and ZSM-38. ZSM-5 is disclosed and claimed in U.S. Pat No. 3,702,886 and U.S. Pat. No. Re. 29,948; ZSM-11 is disclosed and claimed in U.S. Pat. No. 3,709,979. Also, see U.S. Pat. Nos. 3,832,449 for ZSM-12; 4,076,842 for ZSM-23; 4,016,245 for ZSM-35 and 4,046,839 for ZSM-38. The disclosures of these patents are incorporated herein by reference. A suitable shape selective medium pore catalyst for fixed bed is a small crystal H-ZSM-5 zeolite (silica:alumina ratio=70:1) with alumina binder in the form of cylindrical extrudates of about 1-5mm. Unless otherwise stated in this description, the catalyst shall consist essentially of ZSM-5, which has a crystallite size of about 0.02 to 0.05 micron, or ZSM-23. Other pentasil catalysts which may be used in one or more reactor stages include a variety of medium pore siliceous material disclosed in U.S. Pat. Nos. 4,414,423 and 4,417,088, incorporated herein by reference.

The acid atalysts are deactivated by pretreatment with a surface-neutralizin9 base, as disclosed by Chen, et al., and Page, et al., in the patent and allowed application incorporated by reference. Surface deactivation is carried out using bulky or sterically hindered bases, typically those comprising trialkyl substituted pyridines. These hindered bases have very limited access to the internal pore structure of the catalyst, leaving the pores active sites for near linear oligomerization. However, active surface sites which are not constrained, as pores are, to low branching oligomerization are neutralized.

Considering propylene oligomerization for purposes of illustration, the olefinic oligomerization-polymerization products include $C_{10}+$ substantially linear aliphatic hydrocarbons. The ZSM-5 catalytic path for propylene feed provides a long chain with approximately one lower alkyl (e.g., methyl) substituent per 8 or more carbon atoms in the straight chain.

When propylene or butene are oligomerized according to processes described herein, a unique mixture of liquid hydrocarbon products are formed. More particularly, this mixture of hydrocarbons may comprise at least 95% by weight of mono-olefin oligomers of the empirical formula:

$$C_nH_{2n}$$

where n is 3 to 30, the mono-olefin oligomers comprising at least 20 percent by weight of olefins having at least 12 carbon atoms, the olefins having at least 12 carbon atoms having an average of from 0.80 to 2.00 methyl side groups per carbon chain, the olefins not having any side groups other than methyl.

It will be understood that methyl side groups are methyl groups which occupy positions other than the terminal positions of the first and last (i.e., alpha and omega) carbon atoms of the longest carbon chain. This longest carbon chain is also referred to herein as the carbon backbone chain of the olefin. The average number of methyl side groups for the $C_{12}$ olefins may comprise any range with the range of 0.80 to 2.00.

These oligomers may be separated into fractions by conventional distillation separation. When propylene is oligomerized, olefin fractions containing the following number of carbon atoms can be obtained: 6, 9, 12, 15, 18 and 21. When butene is oligomerized, olefin fractions containing the following numbers of carbon atoms may be obtained: 8, 12, 16, 20, 24 and 28. It is also possible to oligomerize a mixture of propylene and butene and to obtain a mixture of oligomers having at least 6 carbon atoms.

Page and Young (allowed Application Ser. No. 105,438, filed Oct. 7, 1987) described these new olefins as multicomponent mixtures of propylene oligomers having relatively few branching methyl groups on the carbon backbone. As an example of branching, the dodecene fraction prepared from propylene and HZSM-23 surface modified by collidine [ZSM -23-dodecenes] typically has 1.3 methyl branches. This can be reduced to 1.0 or less by varying reaction conditions.

Lubricant compositions prepared by the oligomerization of alpha-olefins such as 1-decene under oligomerization conditions in contact with a supported and reduced valence state metal oxide catalyst from Group VIB of the IUPAC Periodic Table are also preferred starting material. CO reduced chromium oxide on silica support is the preferred catalyst. The liquid hydrocarbon lubricant compositions prepared by $C_6-C_{20}$ 1-alkene oligomerization exhibit high viscosity index (VI) and low pour points. The compositions, described in detail in the aforementioned patents of M. WU, comprise $C_{30}-C_{1300}$ hydrocarbons having a branch ratio of less than 0.19; weight average molecular weight between 300 and 45,000; number average molecular weight between 300 and 8,000; molecular weight distribution between 1 and 5 and pour point below $-15°$ C.

Alkenes containing Polar Groups

The co-reactant with the olefinic lube in the present invention comprises an alkene which contains a polar group that will confer a functional utility on the olefinic lube when incorporated into the lube molecule through olefin metathesis. The alkene comprises $C_2+$ olefins and can be a mono-olefin, diolefin or polyolefin. It can be monomeric or polymeric, cyclic or acyclic. However, the alkene must contain a polar functional group, preferably separated from the olefin bond by at least one methylene group.

The term functional group or functionalization as used herein refers to those typically polar organic or organometallic groups, and to their incorporation into lube range molecules, that augment the properties of lubricants by increasing their compatibility with additive packages, or that confer typically additive properties on the lubricant, including but not limited to antiwear properties, anticorrosion, antioxidant, etc.

Useful alkenes in the present invention comprise those containing at least one polar functional group including moieties comprising halogen, hydroxy, alkoxy, aryloxy, carboxy, carboxylate, alkoxycarbonyl, aryloxycarbonyl, amido, imido, cyano, carbonyl, amino, alkylamino, alkylammonium, sulfhydryl, alkylthio, arylthio, dithio, sulfonyl, sulfo, sulfinyl, thiocarbonyl, phosphino, phosphinyl, phospho, phosphono, ureido, nitro, nitroso, silyl, siloxy, and the like. Preferably, the alkenes include olefin $C_3-C_{20}$ carboxylic acids and derivatives thereof, olefinic alcohols, alkenyl esters and tosylates, olefinic ethers and silanes. More preferably, the alkenes include alkyl oleate, alkyl 4-pentenoate, 4-butenylacetate, allylacetate, diallylether, vinyltrimethyl silane and allyloxytrimethyl silane.

Olefin Metathesis Reaction is conversion of olefinic hydrocarbons can be thought of as comprising the breaking of two unsaturated bonds between first and second carbon atoms and between third and fourth carbon atoms of respective olefins with the formation of two new olefinic bonds in different molecules. Olefin metathesis can be carried out between a wide range of unsubstituted, substituted and/or functionalized olefins. For metathesis of nonfunctionalized olefins, the most active catalysts are based on the transitional metals tungsten, molybdenum, and rhenium. Both homogeneous and heterogeneous catalysts have been developed. Van Dam has found (Chem. Soc., Chem. Commun., 1972, 1221) that a catalyst system consisting of $WCl_6$ with $(CH_3)_4Sn$ is effective for the homogeneously catalyzed metathesis of functionalized olefins comprising long chain fatty acid esters. Other examples of catalyst systems and functionalized olefins which will participate in olefin metathesis are found in the cited reference by Ivin and in *Olefin Metathesis and Ring-Opening Polymerization of Cyclo-Olefins* by V. Dragutan, published by John Wiley & Sons Limited, pages 110-113, incorporated herein by reference.

Recently, new catalytic systems have been uncovered to affect metathesis of functionalized olefins as reported by J. C. Mol, Metathesis of Functionalized Olefins, in Chemtech, Apr. 1983, page 250. A functionalized olefin can include those such as unsaturated carboxylic esters, alkenyl esters, ether-containing olefins, nitrogen-containing olefins, halogen-containing olefins or olefins containing both silicon and oxygen.

Suitable conditions for the metathesis reaction include a pressure of from about 0-5000 psig, a temperature of from about ambient to about 1000° F., and space velocities of from about 1 to about 300 WHSV based on the nature of the metathesis catalyst. Although the activity of the catalyst is suitable within the broad ranges mentioned above, increased activity is generally found when the pressure is from about 100 to about 500 psig, the temperature range is from about 650°-850° F., and the WHSV is from about 0.5 to about 1000. The particular temperature, pressure and flow rates utilized within these ranges is largely dependent on the properties of the feed material undergoing the metathesis conversion. The process can be carried out either in the presence or absence of a diluent. Diluents comprising paraffinic and cycloparaffinic hydrocarbons can be employed. Suitable diluents are, for example, propane, cyclohexanes, methycyclohexane, normal pentane, normal hexane, isooctane, dodecane, and the like, or mixtures thereof, including primarily those paraffins and cycloparaffins having up to 12 carbon atoms per molecule. The diluent should be nonreactive under the conditions of the reaction.

The following Examples are presented to illustrate the process of the present invention for the incorporation of functional polar groups into lubricant range olefins by metathesis with alkenes containing polar functional groups. The Examples show reactants, the catalyst system and conditions employed, and the products produced. In these Examples the lubricant grade olefin starting material used, and preferred, is that prepared by the oligomerization of light or lower olefins, particularly propylene, employing surface deactivated ZSM-5 or ZSM-23 prepared according to the aforementioned references of Chen and Page and characterized in the Examples as MOL.

EXAMPLE I

Unsaturated carboxylic esters undergo metathesis when the ester group and carbon-carbon double bond are separated by at least one methylene group. One hundred grams of MOL of an average carbon number of $C_{20}$ to $C_{30}$ mixed with 30 grams of methyloleate are deoxygenated. Under inert atmosphere and with stirring, 1.26 grams $WCl_6$ and 0.54 grams $(CH_3)_4Sn$ (equal molar catalyst and co-catalyst) are introduced and the mixture is slowly heated to 110° C. After 2 hours equilibrium conversion (~50%) is reached. The reaction and products are as follows where $R_1$ is the lubricant hydrocarbon moiety:

$$R_1-CH=CH-R_2 + CH_3(CH_2)_7CH=CH(CH_2)_7COOCH_3$$

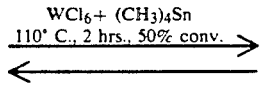

(1) $R_1CH=CH(CH_2)_7COOCH_3$
  +
(2) $R_2-CH=CH(CH_2)_7COOCH_3$
  +
(3) $R_1-CH=CH-R_1$
  +
(4) $R_2-CH=CH-R_2$
  +
(5) $CH_3(CH_2)_7CH=CH(CH_2)_7CH_3$
  +
(6) $H_3COOC(CH_2)_7CH=CH(CH_2)_7COOCH_3$

Although the products 1-6 appear to be numerous they can be categorized as olefins and carboxylic ester-containing olefins. Some products may be less than lube boiling range which can be flashed out and recycled. The lube range products, both functionalized and unfunctionalized, are hydrogenated. The viscosities of the product lube mixtures are 25% to 100% higher and the viscosity index is not substantially changed as compared to the starting lube olefins. The product lubes are compatible with all the polar additives in down stream formulation while the starting lubes are not.

EXAMPLE II

The reaction is carried out using 400 grams of the MOL lube olefin having an average carbon number of $C_{50}$, 80 grams of methyl 4-pentenoate, one gram of $Re_2O_7/Al_2O_3$ (containing 22% $Re_2O_7$ on $Al_2O_3$ activated by heating at 550° C. in a stream of air for 3 hours followed by heating in nitrogen for 1 hr ), and 0.42 ml of $(CH_3)_4Sn$ at 50° C. under an inert atmosphere and 50% conversion is obtained within an hour. In this reaction, ethylene is a product and its removal as a gas favors the reaction equilibrium to the right.

$$R_1-CH=CH_2 + CH_2=CH(CH_2)_2COOCH_3$$

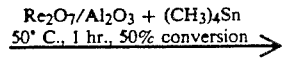

(1) $R_1-CH=CH-R_1$ (2) $CH_2=CH_2$ (3) $R_1-CH=CH(CH_2)_2COOCH_3$ (4) $H_3COOC(CH_2)_2CH=CH(CH_2)_2COOCH_3$

The products are removed of non-lube range materials by flash distillation and finished by hydrogenation of the olefinic double bonds. The functionalized lube mixture is compatible with all polar additives in down stream formulation. They have slightly higher viscosities and essentially the same viscosity indices.

EXAMPLE III

This is an example of co-metathesis between lube olefins and an ester with the double bond in the alcohol fragment (alkenyl esters). Two hundred grams of decene-1 dimer, 1.89 grams of $WCl_6$, 0.81 grams of $(CH_3)_4Sn$, and 60 grams of 4-butenylacetate were reacted at 70° C. in the same experimental set-up as described in Example 1. After 16 hours, a 40% conversion is obtained.

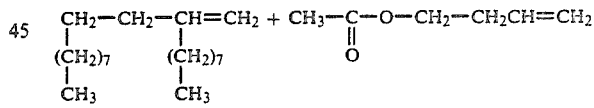

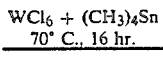

(1) $CH_2-CH_2-CH=CH-CH_2-CH_2-OC-CH_3$ (2) $CH_2=CH_2$

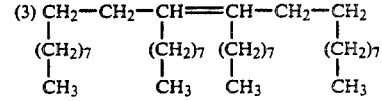

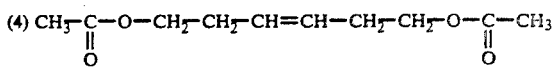

Product (4) may or may not be present in the products since it undergoes further co-metathesis with the decene-1 dimer and with product (3). The product mixture, after the removal of (4) if it is present, has nearly double the starting viscosity but similar viscosity index. The product mixture has significantly higher boiling point range than the starting decene-1 dimer and is compatible with polar additives. It can be used as a lube base stock itself or as a blending component with other lube basestocks.

EXAMPLE IV

Co-metathesis between decene-1 dimer or higher oligomers and allylacetate is effected by using a heterogeneous catalyst system $Re_2O_7/Al_2O_3$-$(CH_3)_4Sn$. When a molar ratio of olefin (200 grams decene-1 dimer + 60 grams allylacetate): Re:Sn = 60:6:1 is used, a conversion of 15-20% is obtained.

EXAMPLE V

Co-metathesis between decene-1 dimer or higher oligomers with diallylether is effected at 90° C. with $Re_2O_7/Al_2O_3$-$(CH_3)_4Sn$ as the catalyst in a molar ratio of olefins (200 grams lube olefin + 60 grams diallylether): Re:Sn = 10:1:3. The equilibrium conversion of 40% is reached at room temperature.

$$R_1CH=CH_2 + CH_2=CH-CH_2-O-CH_2-CH=CH_2$$

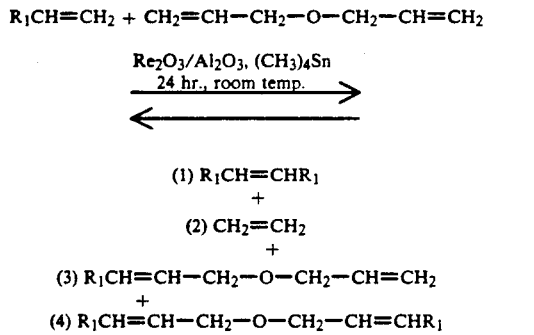

(1) $R_1CH=CHR_1$
+
(2) $CH_2=CH_2$
+
(3) $R_1CH=CH-CH_2-O-CH_2-CH=CH_2$
+
(4) $R_1CH=CH-CH_2-O-CH_2-CH=CHR_1$

EXAMPLE VI

This example describes the introduction of silicon elements into lube olefins.

$$R_1-CH=CH-R_2 + (CH_3)_3SiCH=CH_2$$

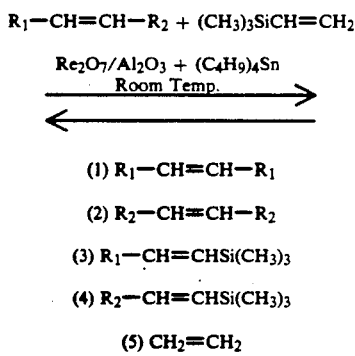

(1) $R_1-CH=CH-R_1$ (2) $R_2-CH=CH-R_2$ (3) $R_1-CH=CHSi(CH_3)_3$ (4) $R_2-CH=CHSi(CH_3)_3$ (5) $CH_2=CH_2$

The resulting lube products have substantially higher viscosity index due to the presence of silicon.

EXAMPLE VII

Olefins containing both silicon and oxygen can also undergo metathesis providing a convenient way of introducing both elements into the lube molecules as shown in this example.

$$R_1CH=CH_2 + CH_2=CHCH_2OSi(CH_3)_3$$

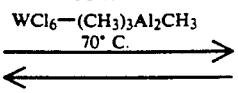

(1) $R_1CH=CH-R_1$
+
(2) $R_1CH=CH-CH_2OSi(CH_3)_3$ (3) $(CH_3)_3SiOCH_2CH=CHCH_2OSi(CH_3)_3$

The product mixture has substantially higher viscosity index than the starting lube olefin. It is alos a special grade of lubricant.

EXAMPLE VIII

This example describes the introduction of the functional group tosylate into the lube molecule.

$$R_1CH=CHR_2 + R_3HC=CH(CH_2)_nOTs$$

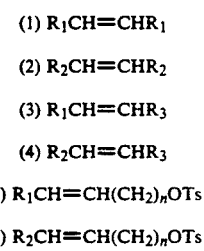

(1) $R_1CH=CHR_1$ (2) $R_2CH=CHR_2$ (3) $R_1CH=CHR_3$ (4) $R_2CH=CHR_3$ (5) $R_1CH=CH(CH_2)_nOTs$ (6) $R_2CH=CH(CH_2)_nOTs$

The novel functionalized lubricants of the present invention may be incorporated as blends with other lubricants and polymer systems in quantities ranging from 0.1 to 100% or may, themselves, be used as additives or in substitution for conventional additives. Lubricants and polymer systems which can be blended with the functionalized lubricants comprise $C_{30}+$ hydrocarbons and lubricants including: mineral oil derived from petroleum; hydrogenated polyolefins comprising polybutylene, polypropylene and higher polyalpha-olefins; polyethers comprising polyethylene gylcol; vinyl polymers comprising polymethylmethacrylate and polyvinylcholoride; polyesters comprising polyethyleneterephthate and polyethyleneadipate; polycarbonates comprising polybisphenol-A carbonate, polyurethanes comprising polyethylenesuccinoylcarbamate; polyacetals comprising polyoxymethylene; and polyamides comprising polycaprolactam.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A process for the production of hydrocarbon lubricant fluid containing one or more polar functional groups, comprising;

contacting a feedstock comprising olefinic hydrocarbon lubricant and at least one alkene containing a polar organic or organometallic functional group with olefin metathesis catalyst under olefin metathesis reaction conditions for a time sufficient to convert a portion of said olefinic hydrocarbon lubricant to one containing said polar functional group; separating the product of said olefin methathesis reaction and recovering a mixture comprising said hydrocarbon lubricant fluid containing at least one polar functional group.

2. The process of claim 1 including the further step of hydrogenating said hydrocarbon lubricant fluid under conditions sufficient to saturate olefinic bonds contained therein.

3. The process of claim 1 wherein said olefinic hydrocarbon lubricant includes $C_{20}+$ hydrocarbons comprising the reaction product of $C_3$–$C_{20}$ alpha olefins in contact with cationic, coordination or acidic shape selective zeolite catalyst.

4. The process of claim 3 wherein said olefinic hydrocarbon lubricant comprises $C_{20}+$ hydrocarbons containing mineral oil.

5. The process of claim 3 wherein said cationic catalyst includes complexes of boron trifluoride or aluminum chloride.

6. The process of claim 3 wherein said coordination catalyst includes Ziegler catalyst or CO reduced chromium oxide on silica catalyst.

7. The process of claim 3 wherein said zeolite catalyst includes ZSM-5.

8. The process of claim 3 wherein said zeolite catalyst includes surface deactivated ZSM-5 or ZSM-23.

9. The process of claim 1 wherein said alkene contains at least one polar functional group including moieties comprising halogen, hydroxy, alkoxy, aryloxy, carboxy, carboxylate, alkoxycarbonyl, aryloxycarbonyl, amido, imido, cyano, carbonyl, amino, alkylamino, alkylammonium, sulfhydryl, alkylthio, arylthio, dithio, sulfonyl, sulfo, sulfinyl, thiocarbonyl, phosphino, phosphinyl, phospho, phosphono, ureido, nitro, nitroso, silyl, siloxy, and the like.

10. The process of claim 1 wherein said alkene includes olefinic $C_3$–$C_{20}$ carboxylic acids and derivatives thereof, olefinic alcohols, alkenyl esters and tosylates, olefinic ethers and silanes.

11. The process of claim 10 wherein said alkene includes alkyl oleate, alkyl 4-pentenoate, 4-butenylacetate, allylacetate, diallylether, vinyltrimethyl silane and allyloxytrimethyl silane.

12. The process of claim 1 wherein said olefin metathesis catalyst includes tungsten halides, tungsten oxyhalides, rhenium oxide on $Al_2O_3$.

13. The process of claim 12 including tetraalkyl tin cocatalyst.

14. The process of claim 13 including tetramethyl tin.

15. The process of claim 12 wherein said tungsten halide comprises $WCL_6$.

16. The product of the process according to claim 1.

17. The product of the process according to claim 1 wherein said
olefinic hydrocarbon lubricant contains slightly branched hydrocarbons comprising the oligomerization product of propylene in contact with surface deactivated ZSM-5 or ZSM-23 catalyst.

18. A hydrocarbon lubricant fluid comprising $C_{30}+$ hydrocarbons and a portion of the product of the process according to claim 1.

19. The lubricant of claim 18 wherein said $C_{30}+$ hydrocarbons include the product of the oligomerization of alpha olefins with cationic or coordination catalyst, or the product of the oligomerization of propylene with zeolite catalyst.

20. The hydrocarbon lubricant fluid of claim 18 further containing additives taken from the group consisting of antioxidants, anticorrosion compounds, wear resistant compounds, solubilizing agents, and the like.

* * * * *